(12) United States Patent
Philippe

(10) Patent No.: US 8,113,424 B2
(45) Date of Patent: Feb. 14, 2012

(54) SYSTEM AND METHOD FOR TRACKING MEDICAL PRODUCTS IN A TWO BIN PER MEDICAL PRODUCT REPLENISHMENT SYSTEM

(75) Inventor: Richard Philippe, Laval (CA)

(73) Assignee: LOGI D Inc., Laval, Quebec (CA)

( * ) Notice: Subject to any disclaimer, the term of this patent is extended or adjusted under 35 U.S.C. 154(b) by 336 days.

(21) Appl. No.: 12/578,683

(22) Filed: Oct. 14, 2009

(65) Prior Publication Data

US 2011/0084135 A1 Apr. 14, 2011

(51) Int. Cl.
| | |
|---|---|
| G08B 13/14 | (2006.01) |
| G05B 19/00 | (2006.01) |
| G06G 1/14 | (2006.01) |
| G06Q 20/00 | (2006.01) |
| G06Q 10/00 | (2006.01) |
| G06Q 30/00 | (2006.01) |
| G06Q 90/00 | (2006.01) |
| G06F 17/00 | (2006.01) |
| G06F 19/00 | (2011.01) |
| G06K 7/08 | (2006.01) |
| G06K 19/00 | (2006.01) |
| G06K 19/06 | (2006.01) |

(52) U.S. Cl. ........ 235/385; 235/375; 235/435; 235/450; 235/451; 235/487; 235/492; 235/493; 705/22; 705/28; 340/572.1; 340/5.92

(58) Field of Classification Search .......... 235/375, 235/385, 435, 450, 451, 487, 492, 493; 705/22, 705/28; 340/5.92, 572.1

See application file for complete search history.

(56) References Cited

U.S. PATENT DOCUMENTS

| | | | | |
|---|---|---|---|---|
| 5,912,818 | A  * | 6/1999 | McGrady et al. | 700/232 |
| 6,112,502 | A  * | 9/2000 | Frederick et al. | 53/411 |
| 7,349,858 | B1 * | 3/2008 | McGrady et al. | 705/3 |
| 7,382,255 | B2 * | 6/2008 | Chung | 340/572.1 |
| 2002/0173875 | A1* | 11/2002 | Wallace et al. | 700/242 |
| 2004/0046020 | A1* | 3/2004 | Andreasson et al. | 235/385 |
| 2004/0133705 | A1* | 7/2004 | Broussard et al. | 710/1 |
| 2005/0110640 | A1* | 5/2005 | Chung | 340/572.1 |
| 2007/0023512 | A1* | 2/2007 | Miller et al. | 235/385 |
| 2007/0208598 | A1* | 9/2007 | McGrady et al. | 705/3 |
| 2007/0272746 | A1* | 11/2007 | Ortiz et al. | 235/385 |
| 2008/0180249 | A1* | 7/2008 | Butler et al. | 340/572.1 |
| 2008/0316045 | A1* | 12/2008 | Sriharto et al. | 340/825.49 |
| 2008/0319577 | A1* | 12/2008 | Vahlberg et al. | 700/241 |
| 2010/0134251 | A1* | 6/2010 | Philippe | 340/5.92 |
| 2011/0105854 | A1* | 5/2011 | Kiani et al. | 600/300 |

* cited by examiner

*Primary Examiner* — Daniel Walsh

(74) *Attorney, Agent, or Firm* — Bereskin & Parr LLP

(57) ABSTRACT

The present relates to a system and method for tracking medical products in a two bin per medical product replenishment system. The system and method comprising storing medical product information including lot number and date of receipt, and recording replenishment requests and generated date. The system and method further correlate the date of receipt of the medical product having the particular medical product information with the generated date of recorded replenishment requests to identify probable corresponding replenishment requests. Also, the system and method correlate identified probable corresponding replenishment requests with location information of corresponding RFID tags to determine corresponding probable locations.

13 Claims, 5 Drawing Sheets

SYSTEM AND METHOD FOR TRACKING MEDICAL PRODUCTS IN A TWO BIN PER MEDICAL PRODUCT REPLENISHMENT SYSTEM

FIELD OF THE INVENTION

The present relates to a system and method for tracking medical products. More particularly, the system and method further relates to tracking products in a two bin per medical product replenishment system.

BACKGROUND OF THE INVENTION

Today's health care facilities include a wide range of establishments, from small and relatively simple medical clinics to large and complex hospitals. All together, health care facilities use a large amount of medical products for treating patients having various health conditions. In some instances, it is required to keep track of products that have been used for treatment, or installed within patients, to ensure compatibility or to readily be able to contact patients for product recalls. More particularly, in large hospitals, keeping track of such products that have been used on or installed within patients is a challenge, as it is performed manually, requires filling multiple forms which is time consuming and limited by practitioners and personal vigilance and discipline. It is thus obvious that such a manual tracking is only performed for specific products which are either more expensive or potentially health dangerous.

In addition to the tracking problem, hospitals also face an important challenge with the management of expiry dates and recalls of lots of medical products. Nowadays, the tracking of expiration dates and recalls of lots of medical products is performed manually. A first control method consists of having a person go through the various medical products at all units and departments to manually check the expiration date and/or the lot number of each medical product, and to remove the medical products which expiration date has lapsed or which lot number has been recalled. As this type of control cannot be performed on a daily or weekly basis, the medical products with the closest expiration date are placed in the front, and the products with the furthest expiration date are placed in the back, to ensure that closely expiring medical products are used first. In addition to this control method, practitioners and personal has to further review prior to using a medical product that the expiration date has not lapsed. Although verification is performed in two steps, there have been reported instances where medical products used were expired or were recalled.

It would therefore be advantageous to have a system and method to more efficiently handle expiration dates and recalls of medical products.

SUMMARY OF THE INVENTION

In accordance with an aspect, the present invention provides a system for tracking medical products in a two bin per medical product replenishment system. The two bin per medical product replenishment system comprises a central unit for linking a unique Radio Frequency Identifier (RFID) tags to a location, a bin and a medical product. The two bin per medical product replenishment system further comprises provisioning boards for generating a provisioning request upon application of one of the unique RFID tags there against. The system for tracking comprises a medical product unit, an RFID tag activity unit and an analysis unit. The medical product unit stores medical product information including lot number and date of receipt. The RFID tag activity unit records replenishment requests and corresponding generated date. The analysis unit determines probable locations of the medical product having particular medical product information in the two bin per medical product replenishment system. For doing so, the analysis unit correlates the date of receipt of the medical product having the particular medical product information with the generated date of recorded replenishment requests, to identify probable corresponding replenishment requests. The analysis unit further correlates the identified probable corresponding replenishment requests with the location information of the corresponding RFID tag in the central unit to determine corresponding probable locations.

In accordance with another aspect, the present invention provides a method for tracking medical products in a two bin per medical product replenishment system. The method comprises storing medical product information including lot number and date of receipt. The method also records replenishment requests and generated date. Then, the method correlates the date of receipt of the medical product having a medical product information of interest with the generated date of recorded replenishment requests, to identify probable corresponding replenishment requests. Finally, the method further correlates the identified probable corresponding replenishment requests with the location information of the corresponding RFID tag in the central unit, to determine corresponding probable locations.

BRIEF DESCRIPTION OF THE DRAWINGS

For a better understanding of aspects of the system and method described herein, and to show more clearly how they may be carried into effect, reference will be made to the accompanying drawings in which.

DETAILED DESCRIPTION OF THE INVENTION

Figure 1:
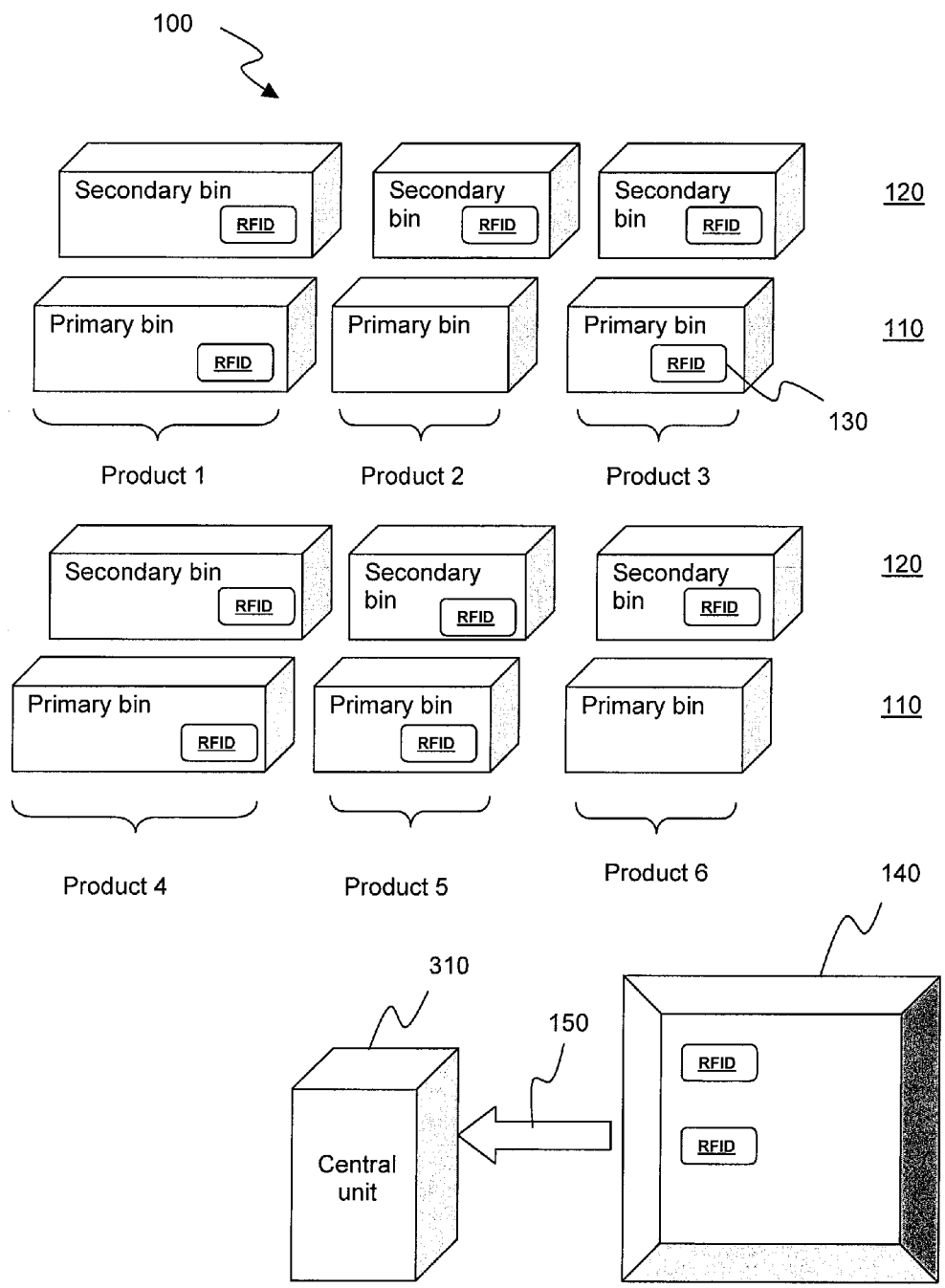
FIG. 1 is a schematic representation of a two bins per medical product replenishment system.

Throughout the present specification, the expression "medical product" is used to refer to any type of product or material to be used or administered in the treatment of patients. Examples of medical products include intravenous solutions, catheters, tubes, etc.

Hospitals are divided in multiple departments, each of which relates to a particular specialization. Each department uses general and specific products, stored in multiple units of the department. Storage is performed using storage equipment that allows the organization of products in two bins, as schematically shown on FIG. 1. Typically in such a system 100, a rack (not shown for clarity purposes), is used to organize storage bins. For each product (products 1-6), a pair of two bins, namely a primary bin 110 and a secondary bin 120 is assigned. The product is thus stored at each location in both the primary 110 and secondary 120 bins. To each primary 110 and secondary 120 bins are associated corresponding removable Radio Frequency Identification (RFID) tags 130. As both primary 110 and secondary 120 bins store a particular product, each RFID tags is unique, and corresponds to a particular product, in a specific bin (primary or secondary), located at a particular location/unit/department in the hospital. When one of the bins becomes empty, the corresponding RFID tag is removed from the bin, as shown for products 2 and 6, and apposed to a provisioning board 140. The RFID tag 130 is usually removed from the bin and applied to the provisioning board 140 by the person emptying or taking the last product in the bin. The provisioning board 140 includes an RFID reader to read the RFID tags 130, and generate provisioning requests 150 therefore to a central unit 310. The provisioning request 150 may be sent by various ways, such as wirelessly, intranet, Internet, etc.

Figure 2:
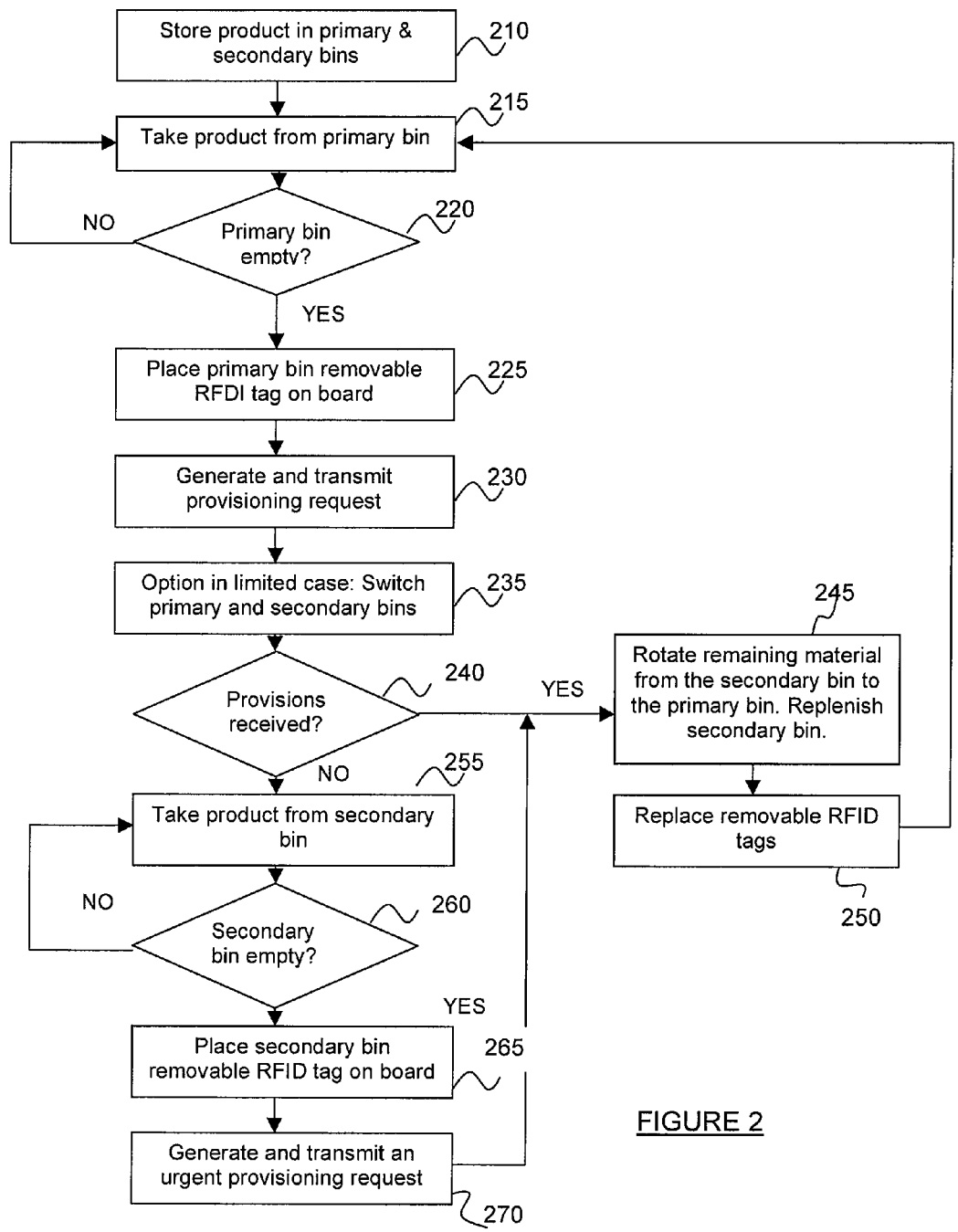
FIG. 2 is a flow chart of a prior art method for provisioning products of a two bins replenishment system with removable RFID tags.

Reference is now concurrently made to FIG. 2, which represents a flowchart of a method for provisioning products in the two bins replenishment system such as shown on FIG. 1. The method starts with storing the product 210 in the corresponding primary 110 and secondary bin 120. Then, in the course of daily activities, the employees of the department take 215, when needed, the product from the primary bin. The employees continue taking the product from the primary bin, until the latter is empty 220. When the primary bin is empty, the employee that takes the last item from the primary bin 110 places 225 the corresponding RFID tag 130 on the provisioning board 140. The provisioning board 140 detects the proximity of the added RFID tag, and generates and transmits 230 a provisioning request 150 for that product. Optionally, it is also possible to switch 235 the primary bin 110 and secondary bin 120 so as to facilitate access to the products in the secondary bin 120.

When provisions are received 240, the method continues with rotating remaining products from the secondary bin to the primary bin, and replenishing 245 the secondary 120 bin (and optionally the primary bin 110). Upon completing the rotation and replenishing of the primary 110 and secondary bins 120, the corresponding RFID tag 130 is removed from the provisioning board 140 and replaced 250 on the corresponding bin. In the event that both the primary bin 110 and secondary bin 120 of a particular product were both empty and had to be replenished, both corresponding RFID tags are removed from the provisioning board 140 and replaced on their respective bin.

In the event that provisions are not received for the empty primary bin 110, when that corresponding product is required, the product is then taken 255 from the secondary bin 120, until the secondary bin 120 becomes also empty 260. When the secondary bin 120 also becomes empty, its removable RFID tag is placed 265 on the provisioning board 140, and an urgent provisioning request 150 is generated and sent 270.

Figure 3:
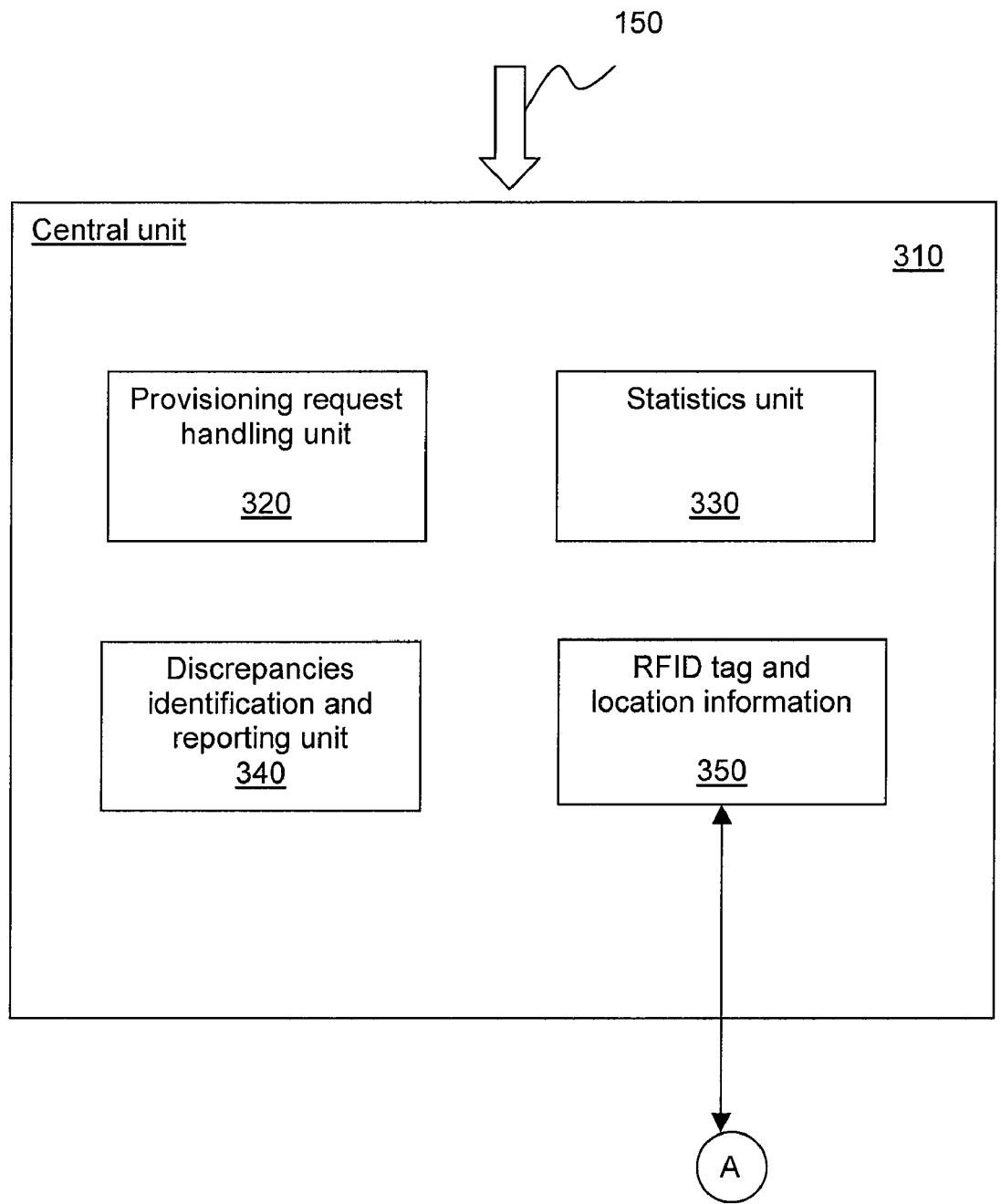
FIG. 3 is an exemplary block diagram of a central unit.

Reference is now made concurrently to FIGS. 1, 2 and 3, where FIG. 3 is a schematic block diagram of an exemplary central unit 310. The central unit 310 is adapted for receiving and handling the provisioning requests 150 for several departments or for a whole hospital. For doing so, the central unit 310 comprises a provisioning request handling unit 320, a statistics unit 330, a discrepancies identification and reporting unit 340 and an RFID tag and location information 350. For clarity purposes, the following components have not been depicted: power unit, communication unit, interface, and input/output unit.

The central unit 310 receives the provisioning requests 150 from provisioning boards 140 located in various departments of the hospital, and the provisioning requests 150 are handled by the provisioning requests handling unit 320. The provisioning requests handling unit 320 compiles the requests, and transfers information in order to generate the provisioning. If the required products are in stock, the provisioning requests handling unit 320 transfers the information to a store or an appropriated department. If the required products are not in stock at a stock room of the hospital, the provisioning requests are transferred to a purchasing department.

The statistics unit 330 calculates for each product used in the hospital a consumption rate per bin, a consumption rate per department, a provisioning rate, and various quotas using the information collected each time a RFID tag 130 has been put on the provisioning board 140 and removed from the provisioning board 140. The statistics unit 330 calculates the various quotas as per the number of day each primary bin 110 and secondary bin 120 should carry. The statistics unit 330 also calculates the various quotas based on replenishment time using the time that a RFID tag 130 is put on a provisioning board 140 to the moment that the RFID tag 130 is placed back on the primary bin 110 or secondary bin 120.

The discrepancies identification unit 340 is adapted to identify, based on the received provisioning requests and calculated statistics, provisioning irregularities. Examples of provisioning irregularities that can be identified by the discrepancies identification unit 340 include: missing RFID tags, duplicate RFID tags, products no longer in use, etc.

The RFID tag and location information unit 350 links each RFID tag 130 to a location (department/unit/room). It further associates the RFID tag 130 to a rack (not shown) in that location, and to a specific bin in the rack. The RFID tag and location information unit 350 further stores information on the product stored in the corresponding bin.

Figure 4:
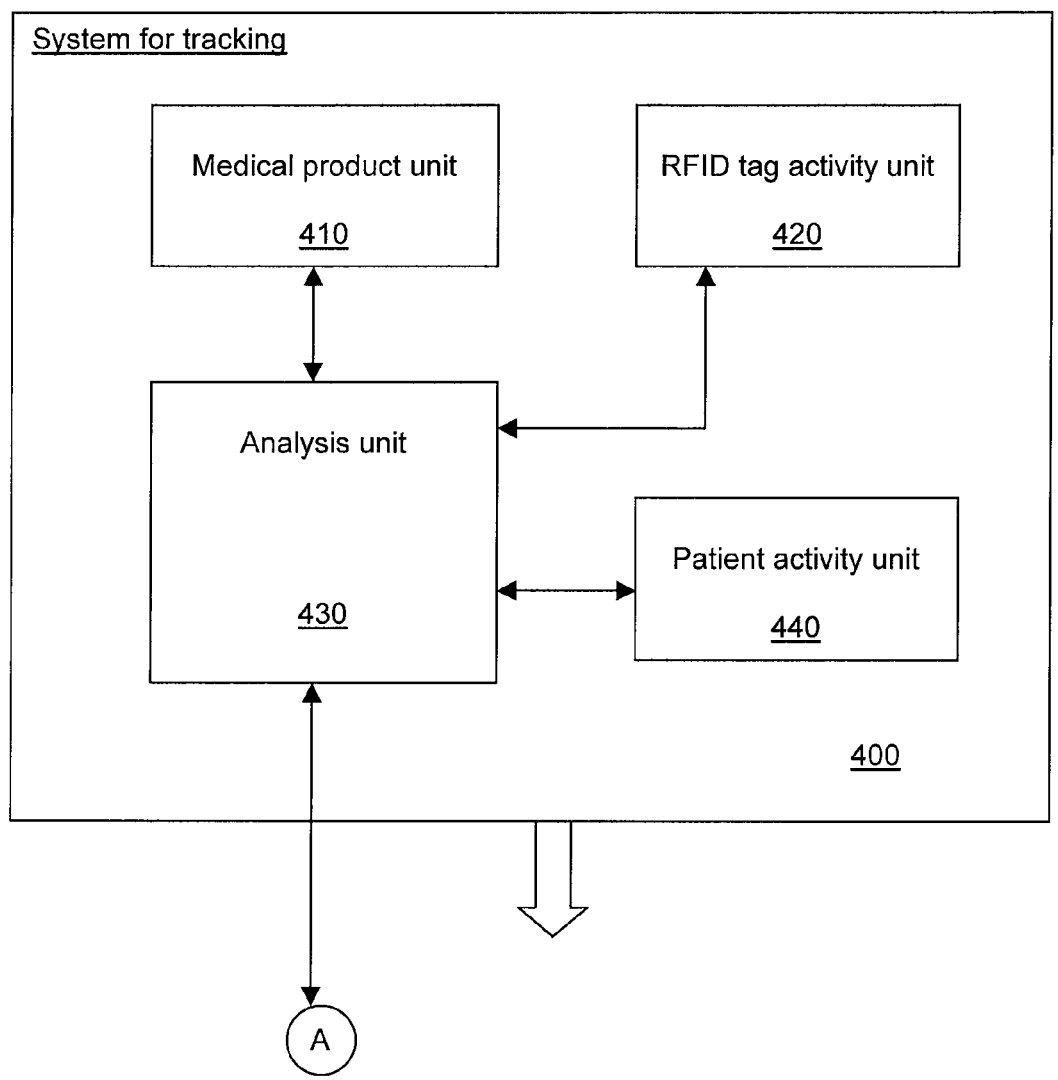
FIG. 4 is an exemplary schematic block diagram of a system for tracking.

Reference is now made to FIG. 4, which is a schematic representation of a system 400 for tracking medical products in the two bin per medical product replenishment system previously described. The system 400 comprises a medical product unit 410, an RFID tag activity unit 420, and analysis unit 430 and a patient activity unit 440. The various units of the system 400 may be implemented concurrently with the central unit 310 or implemented separately. Thus the system for tracking 400 may be sold with the system 100 or separately as an improvement.

The medical product unit 410 stores medical product information for all received medical products. The medical product information comprises lot number and date of receipt. The stored medical product information may further include an expiration date, a quantity, a number of units per box, product code, product serial number if available, product name, a product purchase date, product expiry date, product supplier contact information and product manufacturer's number, etc. The medical product unit 410 stores all necessary product information required for tracking products being recalled: for example by lot #, batch #, serial #, etc.

The RFID tag activity unit 420 records received replenishment requests and date at which they were generated. The RFID tag activity unit 420 may further record the date at which the corresponding bins have been replenished and their RFID tags were removed from the provisioning boards 140.

The patient activity unit 440 is adapted for recording patient identity, location and date of treatment. The patient activity unit 440 may be located as shown on FIG. 4 in the system for tracking 400, or provided by a hospital management database which tracks patient identity, date of treatment, and location in which the treatment was administered.

The analysis unit 430 is adapted for querying the medical product unit 410, the RFID tag activity unit 420 and the patient activity unit 440. The analysis unit 430 determines probable location of medical products having one or several particular medical product information, such as for example:

medical product code, lot #, batch #, date of receipt, expiration date, etc. Tracking specific products in a hospital without the present system requires a lot of manual operations, and depending on the medical product information of interest, may require several days of work, as each bin, each rack, each unit and each department have to be manually checked. However, with the present system and method, probable location of the medical products having the medical product information of interest can be easily determined. The expression "probable location" is used throughout the specification to both include when location is certain and when location is mostly probable. As several medical products are used in multiple units and departments, replenishment of those medical products in the multiple units and departments may be performed on the same day using received products from multiple lot numbers.

When a request is received to track one or several medical products having a particular medical product information, the analysis unit 430 queries the medical product unit 410 to confirm the receiving of a specific medical product having one or several particular medical product information, such as for example: lot #, batch #, date of receipt, expiration date, etc. The analysis unit 430 then gets into communication with the central unit to extract from the RFID tag and location information 350 a list of RFID tags corresponding to tracked medical product(s) and their corresponding location (unit/department/storage rack/bin). The analysis unit 430 also queries the RFID tag activity unit 420 to extract a list of RFID tags corresponding to the product(s) being tracked and generated date of recorded replenishment request. The analysis unit 430 may also query the RFID tag activity unit 420 for extracting all generated replenishment requests recorded corresponding to the product(s) being tracked within a window of time. The window of time may correspond to all replenishment requests received since a prior date of reception for that medical product, or if the amount of medical products received was insufficient to fulfill all replenishment requests, a combination of window of time and rules of delivery may be used to determine the probable replenishment requests.

The analysis unit 430 then correlates particular medical product information of the medical product(s) extracted from the medical product unit 410, with the list of RFID tags extracted from the RFID tag activity unit 420 to determine probable locations. As in the two bin system, the first bin is emptied first, and when emptied the replenishment request is generated for its unique RFID tag, it is possible to identify which bins are awaiting replenishment when the medical product is received. The analysis unit 430 can thus analyze the extracted information from the medical product unit 410, the RFID tag activity unit 420 and the RFID tag and location information based on a set of rules dictated by the two bin per medical product replenishment method.

A first rule is the replenishment of primary and secondary bins. As in step 245 of the method, the remaining medical products are rotated from the secondary bin to the primary bin, although the replenishment request was generated for the primary bin, the analysis unit 430 thus correlates that the replenishment request received for the primary bin results in replenishing the received medical products in its corresponding secondary bin.

Another rule is to determine whether one of the replenishment requests corresponds to the secondary bin. When the replenishment request corresponds to the secondary bin, verification is made as to whether a replenishment request has also been received for the primary bin. In the event that the replenishment request has not been received for the corresponding primary bin, the discrepancy is reported to the discrepancies identification and reporting unit 340.

Another rule applied by the analysis unit is to determine whether the RFID tag activity unit 420 records replenishment date or not. In the event that the date of replenishment is recorded by the RFID tag activity unit 420, upon removal of the RFID tag from the provisioning board, the analysis unit 430 uses the date of replenishment in its analysis for correlating the probable locations.

In the event that some products with a medical product information of interest have already been administered to one or several patients, the present system further allows tracking probable patients to which the medical product has been administered. For doing so, the analysis unit 430 further correlates the probable location and date of the corresponding replenishment requests with the date of treatment recorded in the patient activity unit 440. This aspect allows identifying a window of patients to which the medical product having the medical product information of interest could have been administered. Thus it assists in tracking the probable group of patients to which a medical product having a medical product information of interest, for example a recalled lot number, could have been administered. Although the present system cannot provide an absolute of patients to which the medical product having the medical product information of interest has been administered, it provides a report of probable patients, which is a subset of all patients having been treated during this period.

For doing so, the patient activity unit 440 may record several of the following: a patient number, patient hospital card number, patient medical insurance number, patient name, patient date of birth, patient sex, patient contact information, patient emergency contact information, date of treatment, type of treatment, particular medical products used, etc. The patient activity unit 440 may be embedded within the system for tracking 400, or may be part of a centralized patient system, which the analysis unit 430 may access, and query.

The results of the analysis unit 430 may be provided in the form of a written report, an electronic report, a broadcasted report for handling recalls, a weekly or monthly reported automatically sent to the concerned units/departments or a responsible thereof.

Figure 5:
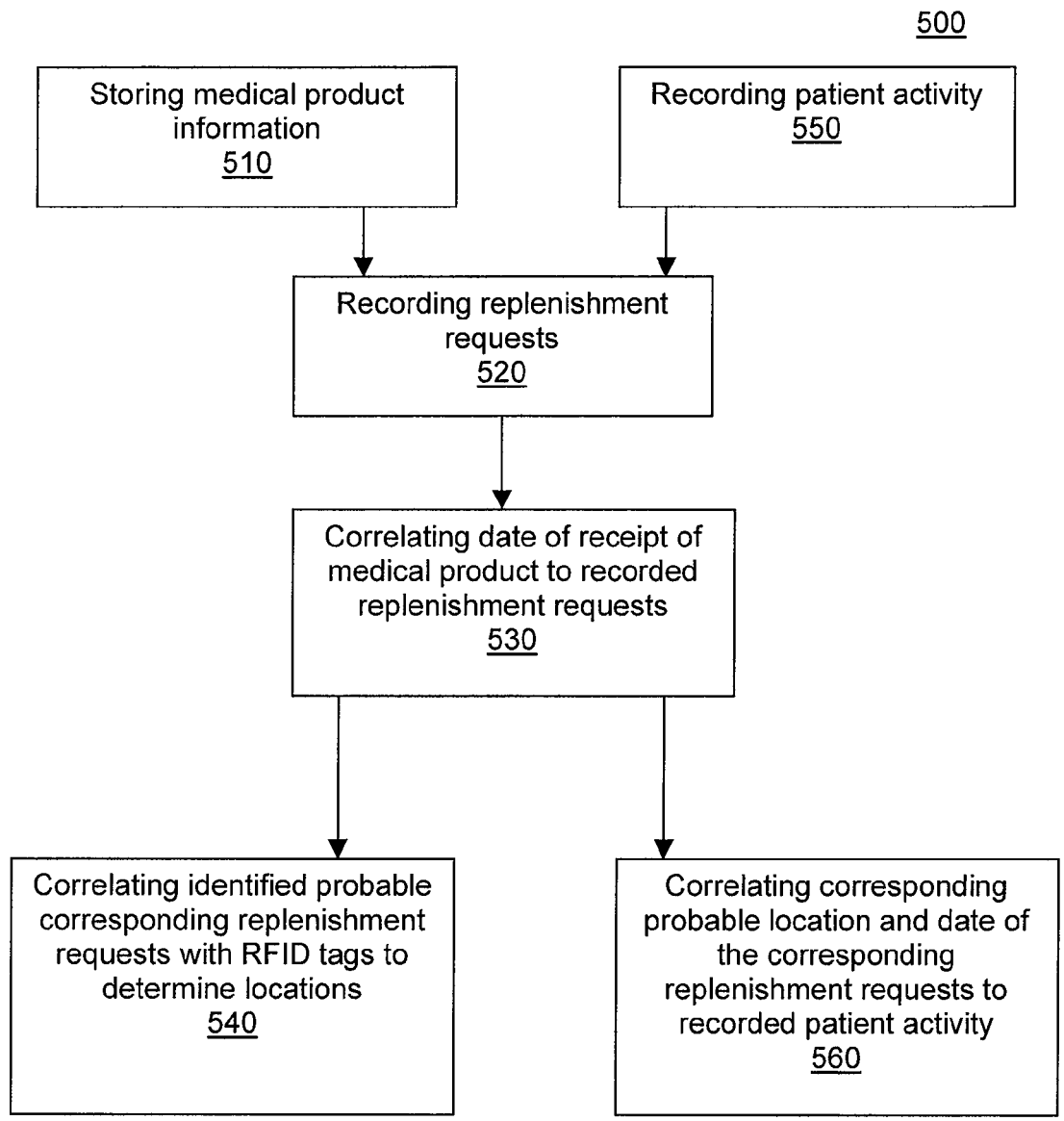
FIG. 5 is an exemplary flowchart of a method for tracking medical products in a two bin per medical product replenishment system.

Reference is now made to FIG. 5, which depicts a flowchart of the method of the present invention. The method starts with storing medical product information 510 in the medical product unit 410. The method continues with recording replenishment requests 520 by the RFID tag activity unit 420. Then, for a medical product information of interest, a correlation is performed of the date of receipt of medical product to recorded replenishment requests 530. The method then correlates the identified probable corresponding replenishment requests with RFID tags to determine probable locations 540.

Alternately, if probable patients to which the medical product having the medical product information of interest have to be identified, the method further records patient activity 550, and correlates corresponding probable location(s) and date(s) of the probable replenishment requests to recorded patient activity.

The present system and method thus allows a simple and efficient way of tracking medical products and corresponding medical product information without adding additional work on medical personnel. Furthermore, the present system and method provides an efficient management tool for handling expiration dates and product recalls. In addition to tracking the medical products with medical product information of interest, the present system and method further assists the medical personnel in identifying groups of probable patients to which the medical product of interest could have been administered.

While the present system and method for tracking have been shown and described with reference to different aspects thereof, it will be recognized by those skilled in the art that various changes in form and detail may be made herein without departing from the spirit and scope of the invention as defined by the appended claims.

The invention claimed is:

1. A system for tracking medical products in a two bin per medical product replenishment system, comprising:
    two bins per medical product, wherein each of the two bins is operable to hold quantities of the medical product;
    a central unit for linking unique Radio Frequency Identifier (RFID) tags to corresponding location, bin and medical product;
    at least one provisioning board for generating a provisioning request upon application of one of the unique RFID tags;
    a medical product unit for storing medical product information including lot number and date of receipt;
    an RFID tag activity unit for recording previous replenishment requests and generated dates of those replenishment requests; and
    an analysis unit for determining probable current locations of a particular medical product in the two bin per medical product replenishment system in response to receipt of a tracking request for the particular medical product, the analysis unit correlating the date of receipt of the particular medical product with the generated date of the previously recorded replenishment requests to identify probable corresponding replenishment requests that might have been filled by the particular medical product, the analysis unit further correlating the identified probable corresponding replenishment requests with the location information of the corresponding RFID tag in the central unit to determine corresponding probable current locations for that particular medical product; and
    a patient activity unit for recording patient identity, location and date of treatment; and wherein:
    the analysis unit further determines probable patients to which the particular medical product having a particular product information has been administered by further correlating the corresponding probable location and date of the corresponding replenishment requests with date of treatment of the patient activity unit to determine probable patients to which the medical product has been administered.

2. The system of claim 1 wherein the medical product unit further stores an expiration date.

3. The system of claim 1 wherein the analysis unit determines the probable location of the particular medical product having a particular lot number.

4. The system of claim 2 wherein the analysis unit determines the probable location of particular medical products having a lapsed expiration date.

5. The system of claim 1 wherein the analysis unit further generates a report of the probable locations.

6. The system of claim 1 wherein the analysis unit is further adapted for querying the medical product unit and the RFID tag activity unit.

7. The system of claim 1 wherein the analysis unit is further adapted for querying the medical product unit, the RFID tag activity unit and the patient activity unit.

8. The system of claim 1 wherein the analysis unit determines probable patients to which the medical product having a particular lot number has been administered.

9. A method of tracking medical products in a two bin per medical product replenishment system, comprising:
    placing quantities of medical products into each of two bins associated with the medical product;
    linking unique Radio Frequency Identifier (RFID) tags to corresponding location, bin and medical product;
    generating a provisioning request upon application of one of the unique RFID tags;
    electronically storing medical product information including lot number and date of receipt;
    electronically recording previous replenishment requests and generated dates of those replenishment requests;
    electronically receiving a tracking request for a particular medical product having a medical product information of interest;
    electronically correlating the date of receipt of the particular medical with the previously recorded generated date of recorded replenishment requests to identify probable corresponding replenishment requests that might have been filled by the particular medical product;
    electronically correlating the identified probable corresponding replenishment requests with the location information of the corresponding RFID tag in the central unit to determine corresponding probable current locations for that particular medical product;
    electronically recording patient activity, the patient activity including identity, location and date of treatment; and
    electronically correlating the corresponding probable location and date of the corresponding replenishment requests with stored date of treatment to determine probable patients to which the particular medical product having the medical product information of interest has possibly been administered.

10. The method of claim 9 wherein the medical product information further includes an expiration date.

11. The method of claim 9 wherein the medical product information of interest is a particular lot number.

12. The method of claim 11 wherein the medical product information is a lapsed expiration date.

13. The method of claim 9 wherein the medical product information of interest is a lot number.

* * * * *